(12) United States Patent
Slavin et al.

(10) Patent No.: US 11,829,456 B1
(45) Date of Patent: Nov. 28, 2023

(54) COMPUTER SYSTEM FOR DELIVERY AND TRACKING ISSUANCE AND USE OF INDIVIDUALIZED INSTANCES OF CONTENT

(71) Applicant: Codebroker, LLC, Belmont, MA (US)

(72) Inventors: Daniel Slavin, Belmont, MA (US); Pero Smrzlic, Leesburg, VA (US)

(73) Assignee: Codebroker, LLC, Belmont, MA (US)

( * ) Notice: Subject to any disclaimer, the term of this patent is extended or adjusted under 35 U.S.C. 154(b) by 0 days.

(21) Appl. No.: 17/123,069

(22) Filed: Dec. 15, 2020

Related U.S. Application Data

(60) Provisional application No. 63/086,545, filed on Oct. 1, 2020, provisional application No. 62/951,359, filed on Dec. 20, 2019.

(51) Int. Cl.
| | | |
|---|---|---|
| *G06Q 30/00* | (2023.01) | |
| *G06F 21/16* | (2013.01) | |
| *G06F 16/28* | (2019.01) | |
| *G06Q 20/20* | (2012.01) | |
| *G06Q 20/38* | (2012.01) | |
| *G06Q 30/0238* | (2023.01) | |
| *G16H 80/00* | (2018.01) | |
| *G16H 20/10* | (2018.01) | |

(52) U.S. Cl.
CPC ............ *G06F 21/16* (2013.01); *G06F 16/288* (2019.01); *G06Q 20/204* (2013.01); *G06Q 20/209* (2013.01); *G06Q 20/387* (2013.01); *G06Q 30/0238* (2013.01); *G06F 2221/0713* (2013.01); *G16H 20/10* (2018.01); *G16H 80/00* (2018.01)

(58) Field of Classification Search
None
See application file for complete search history.

(56) References Cited

U.S. PATENT DOCUMENTS

| | | | | |
|---|---|---|---|---|
| 2004/0236630 | A1* | 11/2004 | Kost | G06Q 30/0222 705/14.23 |
| 2013/0024267 | A1* | 1/2013 | Libenson | G06Q 30/02 705/14.38 |
| 2014/0310063 | A1* | 10/2014 | Freeman | G06Q 30/0205 705/7.34 |
| 2016/0155107 | A1* | 6/2016 | Haijji | G06Q 20/202 705/17 |

* cited by examiner

*Primary Examiner* — Michael W Schmucker
(74) *Attorney, Agent, or Firm* — Patent GC LLC

(57) ABSTRACT

A computer system enables content from a source to be distributed, in some cases through intermediaries, to consumers in a manner that tracks and limits, within preauthorized terms, issuance of individual, unique instances of the content to each respective consumer. Each instance of the content, when distributed through intermediaries, can be unique among the instances of that content distributed by the intermediaries. The computer system tracks issuance, adjudicates and tracks use, such as requests, access, and redemption, of these instances by their respective consumers.

6 Claims, 18 Drawing Sheets

200-Coupons

| Coupon 1 | Group 1 | BIN 1 | PCN 1 | Drug 1 | T&C | etc |
|---|---|---|---|---|---|---|
| Coupon 2 | Group 2 | BIN 2 | PCN 2 | Drug 2 | T&C | etc |

202 - Coupon Codes

| Coupon 1 | Unique ID 1 | Redeemed (count) |
|---|---|---|
| Coupon 1 | Unique ID 2 | Redeemed (count) |
| Coupon 1 | Unique ID 3 | Redeemed (count) |
| Coupon 2 | Unique ID 4 | Redeemed (count) |
| Coupon 2 | Unique ID 5 | Redeemed (count) |

204 - Coupon Code Keywords

| Keyword 1 | Coupon 1 | Unique ID 1 |
|---|---|---|
| Keyword 2 | Coupon 1 | Unique ID 2 |
| Keyword 3 | Coupon 1 | Unique ID 3 |
| Keyword 4 | Coupon 2 | Unique ID 4 |
| Keyword 5 | Coupon 2 | Unique ID 5 |

206 - Coupon Sample Pads

| Pad 1 | Keyword 1 |
|---|---|
| Pad 1 | Keyword 2 |
| Pad 1 | Keyword 3 |
| Pad 2 | Keyword 4 |
| Pad 2 | Keyword 5 |

208 - Coupon URL/Keyword

| URL1 | Keyword 1 |
|---|---|
| URL1 | Keyword 2 |
| URL1 | Keyword 3 |
| URL2 | Keyword 4 |
| URL2 | Keyword 5 |

FIG.2

300 - Physicians

| Physician 1 | Zip Code | etc |
|---|---|---|
| Physician 2 | Zip Code | etc |
| Physician 3 | Zip Code | etc |

302 - Sales Representatives

| Rep 1 | Company 1 | Zip Code | etc |
|---|---|---|---|
| Rep 2 | Company 1 | Zip Code | etc |
| Rep 3 | Company 2 | Zip Code | etc |

304 - Sales Representatives and Physicians

| Rep 1 | Physician 1 |
|---|---|
| Rep 1 | Physician 2 |
| Rep 2 | Physician 2 |
| Rep 3 | Physician 3 |

306 – Sample Request URLs

| Rep 1 | URL1 | Physician 1 | Budget 1 | CurrentCount1 |
|---|---|---|---|---|
| Rep 1 | URL2 | Physician 2 | Budget 2 | CurrentCount2 |
| Rep 2 | URL3 | Physician 2 | Budget 3 | CurrentCount3 |
| Rep 3 | URL4 | Physician 3 | Budget 4 | CurrentCount4 |

308 - Distributed Pads

| Rep 1 | Pad 1 | Physician 1 |
|---|---|---|
| Rep 1 | Pad 2 | Physician 2 |

310 - Consumers

| Phone 1 | Carrier 1 |
|---|---|
| Phone 2 | Carrier 1 |
| Phone 3 | Carrier 2 |

312 - Consumer SMS

| Message 1 | Phone 1 | Coupon 1 | Timestamp | Content |
|---|---|---|---|---|
| Message 2 | Phone 2 | Coupon 2 | Timestamp | Content |

314 - Consumer Coupon Views

| View 1 | Phone 1 | Coupon 1 | Timestamp | IP | Device | Location |
|---|---|---|---|---|---|---|
| View 2 | Phone 2 | Coupon 2 | Timestamp | IP | Device | Location |

| Coupon Server Record ||| 
|---|---|---|
| Physician NPI# | Pharma Co. | Sales Rep ID |
| Pad ID | Physican zip | Grp#, BIN#, PCN# |
| Keyword 1 | Keyword 2 | Keyword 3 | Keyword 4 |
| Unique ID1 | Unique ID2 | Unique ID3 | Unique ID4 |

502

| Coupon Server Record ||||
|---|---|---|---|
| Unique ID1 ||||
| Phone number, Mobile carrier ||||
| Keyword 1 | Msg + Link | Drug name | Other in/ out texts |
| Phone type | IP address | Form View Time/Date | Phone type |
| Form Submit Time/Date | Form name | Program Name | Consent Received |

420
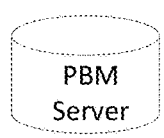
PBM Server

1. Grp#
2. PCN#
3. BIN#
4. Unique ID's

422
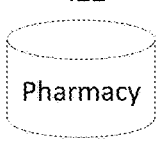
Pharmacy

Pre form submission
1. Time/date of form view(s)
2. Phone type
3. IP address

Post form submission
1. Time/date of form submit

424
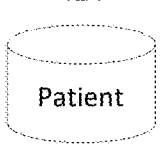
Patient

600-C1 →

426
Coupon Server

← 600-C2
Optional
1. SMS subscription confirmation message

1. Messages
2. Drug name
3. Links

428
Pharma Co.

430
Pharma Sales Rep

432
Physician

Pads
1. Pad Identifier
2. Unique keywords

| Coupon Server Record |||  |
|---|---|---|---|
| Physician NPI# | | Pharma Co. | Sales Rep ID |
| Pad ID | | Physican zip | Grp#, BIN#, PCN# |
| Keyword 1 | Keyword 2 | Keyword 3 | Keyword 4 |
| Unique ID1 | Unique ID2 | Unique ID3 | Unique ID4 |

502

| Coupon Server Record | | | |
|---|---|---|---|
| Unique ID1 ||||
| Phone number, Mobile carrier ||||
| Keyword 1 | Msg + Link | Drug name | Other in/out texts |
| Phone type | IP address | Form View Time/Date | Phone type |
| Form Submit Time/Date | Form name | Program Name | Consent Received |
| SMS Opt-in | | | |

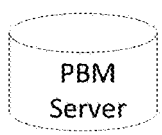

420

1. Grp#
2. PCN#
3. BIN#
4. Unique ID's

PBM Server

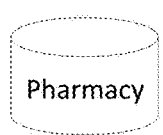

422

Pharmacy

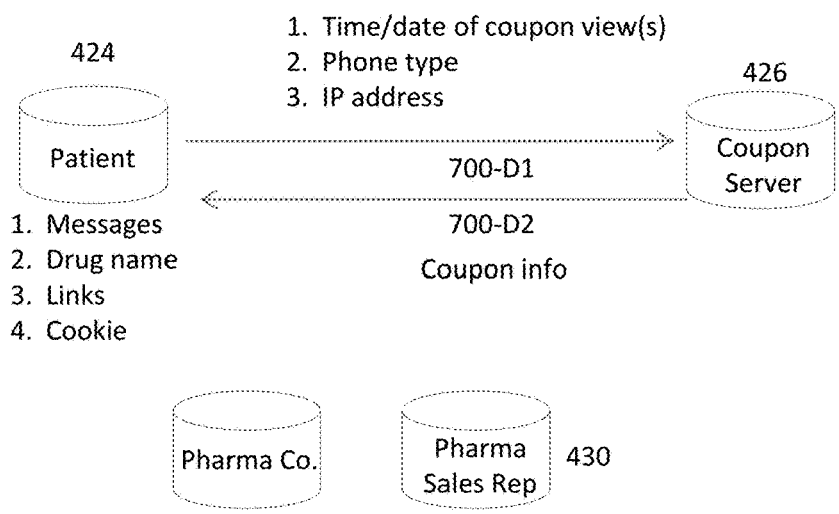

424 Patient

1. Time/date of coupon view(s)
2. Phone type
3. IP address

700-D1 →
← 700-D2
Coupon info

426 Coupon Server

1. Messages
2. Drug name
3. Links
4. Cookie

428 Pharma Co.

430 Pharma Sales Rep

432 Physician

Pads
1. Pad Identifier
2. Unique keywords

Coupon Server Record

| Physician NPI# | Pharma Co. | Sales Rep ID |
|---|---|---|
| Pad ID | Physican zip | Grp#, BIN#, PCN# |
| Keyword 1 | Keyword 2 | Keyword 3 | Keyword 4 |
| Unique ID1 | Unique ID2 | Unique ID3 | Unique ID4 |

502

Coupon Server Record

| Unique ID1 | | | |
|---|---|---|---|
| Phone number, Mobile carrier | | | |
| Keyword 1 | Msg + Link | Drug name | Other in/out texts |
| Phone type | IP address | Form View Time/Date | Phone type |
| Form Submit Time/Date | Form name | Program Name | Consent Received |
| SMS Opt-in | Reminder Text | | |

420
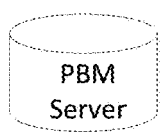
PBM Server

1. Grp#
2. PCN#
3. BIN#
4. Unique ID's

422
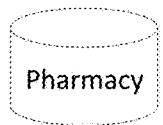
Pharmacy

424
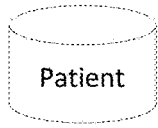
Patient

800- E1

1. Text message reminder

426
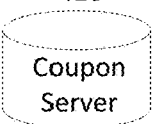
Coupon Server

1. Messages
2. Drug name
3. Links
4. Cookie

428
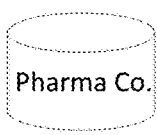
Pharma Co.

430
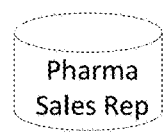
Pharma Sales Rep

432
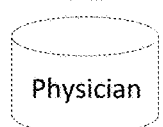
Physician

Pads
1. Pad Identifier
2. Unique keywords

Coupon Server Record

| Physician NPI# | Pharma Co. | Sales Rep ID | |
|---|---|---|---|
| Pad ID | Physican zip | Grp#, BIN#, PCN# | |
| Keyword 1 | Keyword 2 | Keyword 3 | Keyword 4 |
| Unique ID1 | Unique ID2 | Unique ID3 | Unique ID4 |

502

Coupon Server Record

| Unique ID1 | | | | |
|---|---|---|---|---|
| Phone number, Mobile carrier | | | | |
| Keyword 1 | Msg + Link | Drug name | Other in/ out texts | Pharmacy Location |
| Phone type | IP address | Form View Time/Date | Phone type | New Coupon Message |
| Form Submit Time/Date | Form name | Program Name | Consent Received | New Coupon |
| SMS Opt-in | Reminder Text | Coupon Redeemed | Redeeming Pharmacy | |

1. Grp#
2. PCN#
3. BIN#
4. Unique ID's
5. Rx
6. Redemption

420

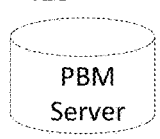

PBM Server

422

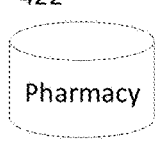

Pharmacy

1. Grp#
2. PCN#
3. BIN#
4. Unique ID's
5. Rx
6. Redemption

424

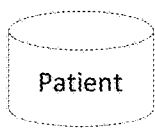

Patient

1. Messages
2. Drug name
3. Links
4. Cookie

1000-G1
1. Text message
2. Link to new coupon

426

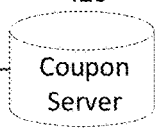

Coupon Server

Pharma Co.

428

Pharma Sales Rep

430

432

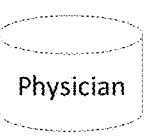

Physician

Pads
1. Pad Identifier
2. Unique keywords

| Coupon Server Record |||||
|---|---|---|---|---|
| Physician NPI# || Pharma Co. || Sales Rep ID |
| Pad ID || Physican zip || Grp#, BIN#, PCN# |
| Keyword 1 | Keyword 2 || Keyword 3 | Keyword 4 |
| Unique ID1 | Unique ID2 || Unique ID3 | Unique ID4 |

502

| Coupon Server Record |||||
|---|---|---|---|---|
| Unique ID1 |||||
| Phone number, Mobile carrier |||||
| Keyword 1 | Msg + Link | Drug name | Other in/ out texts | Pharmacy Location |
| Phone type | IP address | Form View Time/Date | Phone type | New Coupon Message |
| Form Submit Time/Date | Form name | Program Name | Consent Received | New Coupon |
| SMS Opt-in | Reminder Text | Coupon Redeemed | Redeeming Pharmacy ||

1. Grp#
2. PCN#
3. BIN#
4. Unique ID's
5. Rx
6. Redemption

420
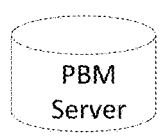
PBM Server

422
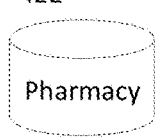
Pharmacy

1. Grp#
2. PCN#
3. BIN#
4. Unique ID's
5. Rx
6. Redemption

424
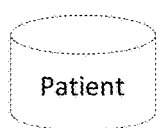
Patient

1. Messages
2. Drug name
3. Links
4. Cookie

1100-H1

Charts, reports

426
Coupon Server

432
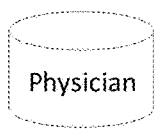
Physician

Pads
1. Pad Identifier
2. Unique keywords

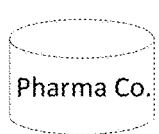
Pharma Co.

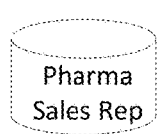
Pharma Sales Rep 428       430

FIG.4H

700
Back of Sample Pad
Pfizer Sample Pad# AGT654
702
 Scan this code with your Smartphone and
704 enter your Sales ID and the Physician's NPI#
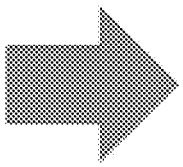
706
Web Form in CB System
Pfizer Sample Pad# AGT654
Tracking Form
Your Sales ID#
708
Physician's NPI#
710
 712
FIG. 7

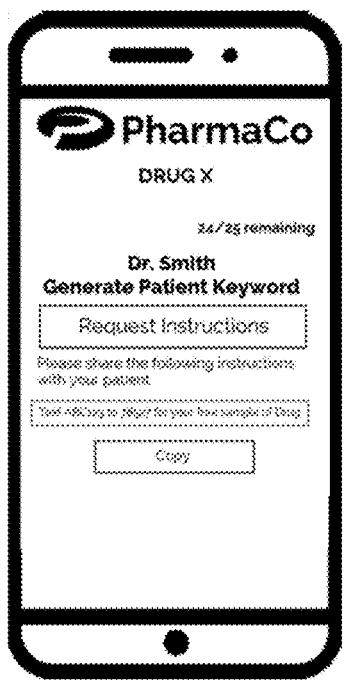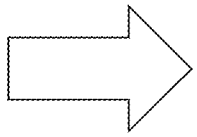
FIG. 9

COMPUTER SYSTEM FOR DELIVERY AND TRACKING ISSUANCE AND USE OF INDIVIDUALIZED INSTANCES OF CONTENT

CROSS REFERENCE TO RELATED APPLICATIONS

This application claims priority to, and is a nonprovisional application of, prior filed provisional applications 62/951,359, filed Dec. 20, 2019, and 63/086,545, filed Oct. 1, 2020, which are hereby incorporated by reference.

BACKGROUND

In many computer-connected systems, one organization acts as a source of content which is distributed to others who use that content. In some cases, content is issued to an individual for their sole use and, in some cases, for a single use. Thus, individuals receive their own individualized or personalized instances of that content. In some cases, the organization may wish to issue that content indirectly, through another trusted party. The organization authorizes one or more trusted parties who in turn issue individualized instances of the content to individuals selected by the trusted parties. In a computer-connected system, technological measures can be used to monitor and track both issuance and subsequent use of these instances of content. Where such individualized instances of content are issued and used digitally, in the form of digital content, in a computer-connected system, technological measures are used to monitor and track both issuance and subsequent use of these instances of digital content.

In some cases, the use of an instance of the content enables access to information, a place, a product, a service, or other thing of value from the organization, one of the trusted parties, or yet another entity. For example, the content may be a coupon, a voucher, a gift card, or loyalty card, or any other content intended to be used by its recipient, whether in the form of a physical item or in electronic form, such as data representing a barcode, a link, an image or any other data in human or machine-readable form. The individual receiving that content may present the content to another party as part of a transaction, such as to purchase or receive a product or service.

As an example, medications are often delivered by pharmaceutical companies to patients through health care providers (HCP's). Currently, there are generally two methods such delivery occurs.

In a first method, a pharmaceutical company delivers physical samples to HCPs. This method is costly, requires extensive tracking, enables HCPs to give patients a relatively unlimited number of samples, does not allow the pharmaceutical manufacturer to track how many samples an HCP gives out and how many of them turn into prescriptions, makes it difficult to track the performance of the sales people that are working with the HCPs, and provides no way for the pharmaceutical manufacturer to deliver follow on messaging to the patient to improve conversions.

In a second method, a plastic or paper sample coupon card is given to a patient by the HCP, which the patient redeems at a pharmacy. This method requires the HCP to physically deliver something to the patient. Usually, the patient is required to register in order to use the sample card. This method typically does not allow for follow on messaging to be delivered to the patent unless the patient completes a formal registration process. This method typically requires the patient to remember to bring the plastic or paper sample card with them to the pharmacy.

These two methods do not address all of the needs of the pharmaceutical manufacturers to i) enable HCP's to provide patients with samples when the HCP does not physically meet with the patient, ii) track and control the distribution of samples and track performance by their sales people and individual HCPs, iii) make it easy for the patient to provide the pharmaceutical manufacturer with the information required to deliver follow up reminders and offers and improve conversion, and iv) to provide a low-friction, mobile-first patient experience.

SUMMARY

This Summary introduces a selection of concepts in simplified form that are described further below in the Detailed Description. This Summary neither identifies key or essential features, nor limits the scope, of the claimed subject matter.

A computer system enables content from a source to be distributed, in some cases through intermediaries, to consumers in a manner that tracks and limits, within preauthorized terms, issuance of individual, unique instances of the content to each respective consumer. Each instance of the content, when distributed through intermediaries, can be unique among the instances of that content distributed by the intermediaries. The computer system tracks issuance and adjudicates and tracks use, such as requests, access, and redemption, of these instances by their respective consumers.

A computer system includes a server system having a resource accessible on a computer network with a resource identifier. For example, a web server can be accessible over the internet, in which case the resource identifier can be a "link", such as a uniform resource locator (URL) or other uniform resource identifier (URI). The server system has a set of request identifiers associated with the resource identifier, and tracks, in a database, an association between the resource identifier and the set of request identifiers associated with the resource identifier. The request identifiers can be any set of unique identifiers, such as keywords or any string of characters, including alphanumeric characters and symbols, or any other information, whether human-readable or machine-readable that can serve to uniquely distinguish one request from another.

The computer system also includes a first consumer device and a second consumer device, wherein the server system, the first consumer device, and the second consumer device communicate over one or more communication networks. The first consumer device is a device used by a trusted party of an entity that is the source of digital content to be distributed. For example, this trusted party may be a health care provider (HCP) that has been authorized by an entity such as a pharmaceutical company to distribute vouchers for samples. The second consumer device is a device used by a party that receives a unique instance of digital content. There typically will be a plurality of first consumer devices and a plurality of second consumer devices.

The server system causes the resource identifier to be distributed to the first consumer device. The first consumer device accesses the resource indicated by the resource identifier. In response to accessing the resource, the first consumer device receives a request identifier from the set of request identifiers associated with the resource identifier. Request identifiers received by the first consumer device are unique to the first consumer device. Other first consumer devices that receive request identifiers are given different respective resource identifiers to access their respective request identifiers. If different resource identifiers are given to different first consumer devices, then the combination of resource identifiers and request identifiers will be unique.

The second consumer device receives a request identifier sent to the first consumer device. This receipt can occur in many ways. A message can be sent from the first consumer device to the second consumer device including the request identifier. The trusted party that controls the first consumer device can otherwise communicate the request identifier to the party that controls the second consumer device through any other channel. This communication can occur electronically directly from the first consumer device to the second consumer device, or using a human form of communication between the two parties, or other physical transfer of the information from one device to the other device. The request identifier, received by the party that controls the second consumer device, can be entered into the second consumer device.

The second consumer device then sends a message over the communication network to the server system, wherein the message includes the received request identifier. This message can be sent through any of a variety of communication channels, such as by, but not limited to, sending a text message, sending electronic mail, or accessing a resource such as a web page. In response to sending the message, the second consumer device receives a content identifier for an instance of digital content. The content identifier corresponds to the received request identifier. This content identifier can be in the form of a link or other data that can be used to access the instance of digital content, or may be an instance of the digital content itself, such as a barcode, image, a sequence of characters, or other data or information that can be presented to a machine or individual.

In response to receiving the message including the received request identifier from the second consumer device, the server system associates the first consumer device, to which the request identifier was unique, and the second consumer device, which received and submitted that request identifier, with the content identifier for the instance of the digital content delivered to the second consumer device. Thus, the server system associates an instance of digital content with the recipient of that instance and other information that tracks how that instance was distributed to the recipient.

The content identifier can be unique to the second consumer device. In some implementations, the content identifier is a link or other kind of resource identifier to access a resource on a server computer connected to the communication network. In response to accessing the resource using the link, the second consumer device receives content associated with the link. The received content can be unique to the second consumer device. The received content can be an instance of the digital content itself. The received content can be a barcode or other information for use at a point of sale. For example, for a pharmaceutical sample, the received content may be a combination one or more of a group number, BIN number, PCN number, or optionally additional identifiers corresponding to a voucher for a prescribed sample.

In some implementations, the server system comprises a digital content delivery and tracking system and an adjudication server. The adjudication server stores information about the instances of digital content for validation of presented instances of digital content. The digital content delivery and tracking system stores information about instances of digital content for tracking distribution of the instances of digital content. In some implementations, the computer system can include or may be connected to a point of sale server. The point of sale server, in response to presentation of content from the second consumer device, sends data about the content to the adjudication server for adjudication.

In some implementations, the computer system further includes a third consumer device communicating on the one or more communication networks. The third consumer device may be used by a party or entity who, for example, authorizes the trusted parties who use the first consumer devices. An example of such a party is a sales representative of a pharmaceutical company that will authorize health care providers to distribute pharmaceutical samples to their patients. The third consumer device receives a plurality of resource identifiers associated with different sets of request identifiers. The sales representative may access an interface of the system to register their own identifier and physician identifiers (e.g., NPI #'s) to associate them with the new resource identifiers. The third consumer device sends one of the resource identifiers from among the plurality of resource identifiers to the first consumer device. Other, different resource identifiers may be sent to other first consumer devices. In response to receiving the message including a received request identifier from the second consumer device, the server system associates the third consumer device, the first consumer device, and the second consumer device with the instance of the digital content delivered to the second consumer device.

In some implementations, the adjudication server does not have unique identifiers for validating instances of digital content presented at a point of sale after distribution by the digital content delivery and tracking system. It thus relies on the digital content delivery and tracking system to generate such unique identifiers. In such implementations, the adjudication server sends information about instances of digital content to the digital content delivery and tracking system. In response to receiving the information about the instances of digital content, the digital content delivery and tracking system generates unique identifiers for the instances of digital content and provides these unique identifiers back to the adjudication server. The adjudication server associates these unique identifiers with the other information it already has about the instances of digital content. In some implementations, the adjudication server generates unique identifiers for validating instances of digital content presented at a point of sale after distribution by the digital content delivery and tracking system. It associates these unique identifiers with information about instances of digital content. It then delivers these unique identifiers along with information about instances of digital content to the digital content delivery and tracking system. In some implementations, these unique identifiers can be part of the instance of the digital content which is delivered to and presented by the consumer device, such as a unique sequence of characters, data that generates and is read from a barcode, or other data which the point of sale would extract from the content presented by the consumer device and send to the adjudication server for validation. These are example mechanisms through which independent adjudication servers and digital content delivery and tracking systems can maintain consistent versions of information.

In some implementations, the digital content delivery and tracking system generates resource identifiers associated with sets of request identifiers and causes a resource identifier to be distributed to the first consumer device or the third consumer device.

In another aspect, the different content items distributed to consumers can be in the form of paper. For example, a health care provider may provide a piece of paper or other suitable material to a patient, that the patient can use to receive a sample of a pharmaceutical. In such an implementation, the computer system includes a server system that includes a database that tracks an association between each of a plurality of resource identifiers and a respective set of request identifiers associated with the resource identifier. A printing system receives data from the database and prints a set of printed items. In the context of the pharmaceutical samples example herein, such a set of printed items is manufactured in the form of a pad of papers, and is called a sample pad. Each set of printed items corresponds to a respective resource identifier among the plurality of resource identifiers, and each item in the set includes a respective request identifier from a set of request identifiers associated with the resource identifier for the set of printed items. Different sets of printed items are distributed to different respective third parties, such as different health care providers each receiving their own respective different sample pads. Each third party can be associated in the database with the resource identifier of the respective set of printed items distributed to that third party.

In this example, the third parties provide printed items from their respective sets to consumers. A consumer has a consumer device. The consumer device communicates with the server system over one or more communication networks. The consumer device receives a request identifier as printed on a printed item, for example by its operator entering the request identifier into the device. The consumer device sends a message including the received request identifier to the server system. In response to sending the message, the consumer device receives a content identifier for an instance of digital content, wherein the content identifier corresponds to the received request identifier. In response to receiving the message including the received request identifier from the consumer device, the server system associates the third party associated with the set of items from which the received request identifier originated and the consumer device with content identifier delivered to the consumer device.

In some implementations, another entity such as a sales representative distributes the set of printed items to the third party, such as a health care provider. In some implementations a representative device, used by the sales representative, also communicates on the one or more communication networks. Through the representative's device, a message is sent to the server system, including data indicating a pad identifier for a set of printed items and data indicating the third party to which the set of printed items corresponding to the pad identifier was distributed and optionally additional identifiers such as an identifier representing the sales representative. In response to receiving the message including a received request identifier from a consumer device, the server system further associates the entity associated with the representative's device with the third party, the consumer device, and the instance of the digital content delivered to the consumer device.

In some implementations, a computer system for management of sample distribution addresses needs of pharmaceutical manufacturers by: controlling distribution so that patients may not receive more than one sample; tracking distribution and redemption by physician and sales person; and obtaining a legally binding opt-in to send follow up reminder and related messages without requiring the patient to enter any demographic data or method of communication. The computer system also may enable the pharmaceutical manufacturer to set rules regarding how frequently a patient can obtain a sample; enable all of the above without requiring the patient to download an app to their mobile device; enable a patient to obtain a coupon for a sample and store it on their mobile device, or enable HCP's to provide their patients with samples without an in-person meeting, or any combination of these.

The following Detailed Description references the accompanying drawings which form a part this application, and which show, by way of illustration, specific example implementations. Other implementations may be made without departing from the scope of the disclosure.

BRIEF DESCRIPTION OF THE DRAWINGS

FIG. 2 is an illustrative example of some data structures for the computer system.

FIG. 3 is an illustrative example of some data structures for the computer system.

FIGS. 4A-4I are drawings illustrating various processing steps performed by the system.

FIG. 7 is a drawing of example content on the back of a sample pad, and example content on a corresponding registration page for sales representatives.

FIGS. 8 and 9 illustrate a contactless approach to delivering content to physicians and from physicians to patients.

DETAILED DESCRIPTION

A computer system enables digital content from a source to be distributed, in some cases through intermediaries, to consumers in a manner that tracks and limits, within preauthorized terms, issuance of individual, unique instances of the digital content to each respective consumer. Each instance of the digital content, when distributed through intermediaries, is unique among instances of that digital content distributed by the intermediaries. The computer system tracks issuance, adjudicates and tracks use, such as requests, access, and redemption, of these instances by their respective consumers.

Figure 1A:
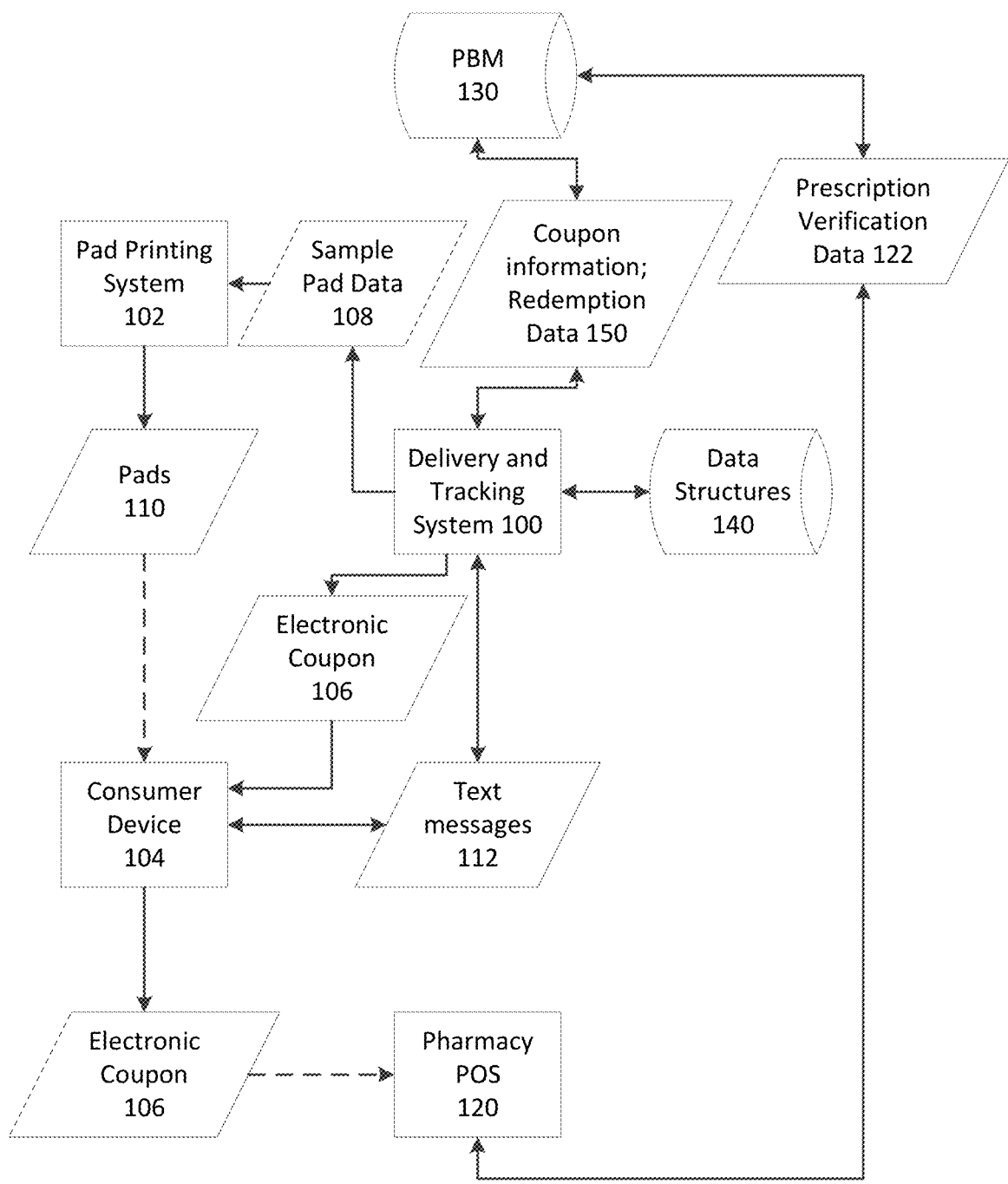
FIG. 1A is a block diagram of an example implementation of a computer system for delivery and tracking of pharmaceutical samples.

Referring to FIG. 1A, an illustrative example of such a computer system as used for delivery and tracking of pharmaceutical samples will be described. In this example, the content delivered is a form of a coupon allowing redemption of a sample of a pharmaceutical. In some implementations, the coupon may be a physical item, such as a piece of paper. In some implementations, the coupon may be in the form of digital content distributed and processed through various computing devices. In this example, in which the content allows access to a pharmaceutical sample, physicians act as trusted parties authorizing patients to receive the content, and the physicians are authorized by the source of the pharmaceutical sample. Each step of the distribution and use of the content, in this case a coupon, is tracked by a computer system to ensure issuance and use are authorized.

In this example implementation, a delivery and tracking system 100 generates sample pad data 108 to a pad printing system 102. The pad printing system manufactures sample pads 110, which is a pad of physical coupons. This sample pad is an example of a set of printed items. The physical coupons include information indicating a keyword to be texted to a number to obtain a coupon. Each sample pad is unique from other sample pads in some way. Each set of printed items, and thus each sample pad, has a respective pad identifier. The physical coupons in a sample pad can all be the same or unique from every other coupon in the sample pad or unique from every other coupon in all other sample pads. The sample pad data 108 provided by the delivery and tracking system 100 ensures the uniqueness of each sample pad, as described in more detail below. A patient is given a physical coupon from a sample pad. A consumer device 104, such as a mobile phone used by a patient, is used by the patient to send a text message 112 including the keyword indicated on a physical coupon to the text number provided on the physical coupon. The delivery and tracking system 100 processes the text message 112 to provide an electronic coupon 106 to the consumer device 104.

Figure 1B:
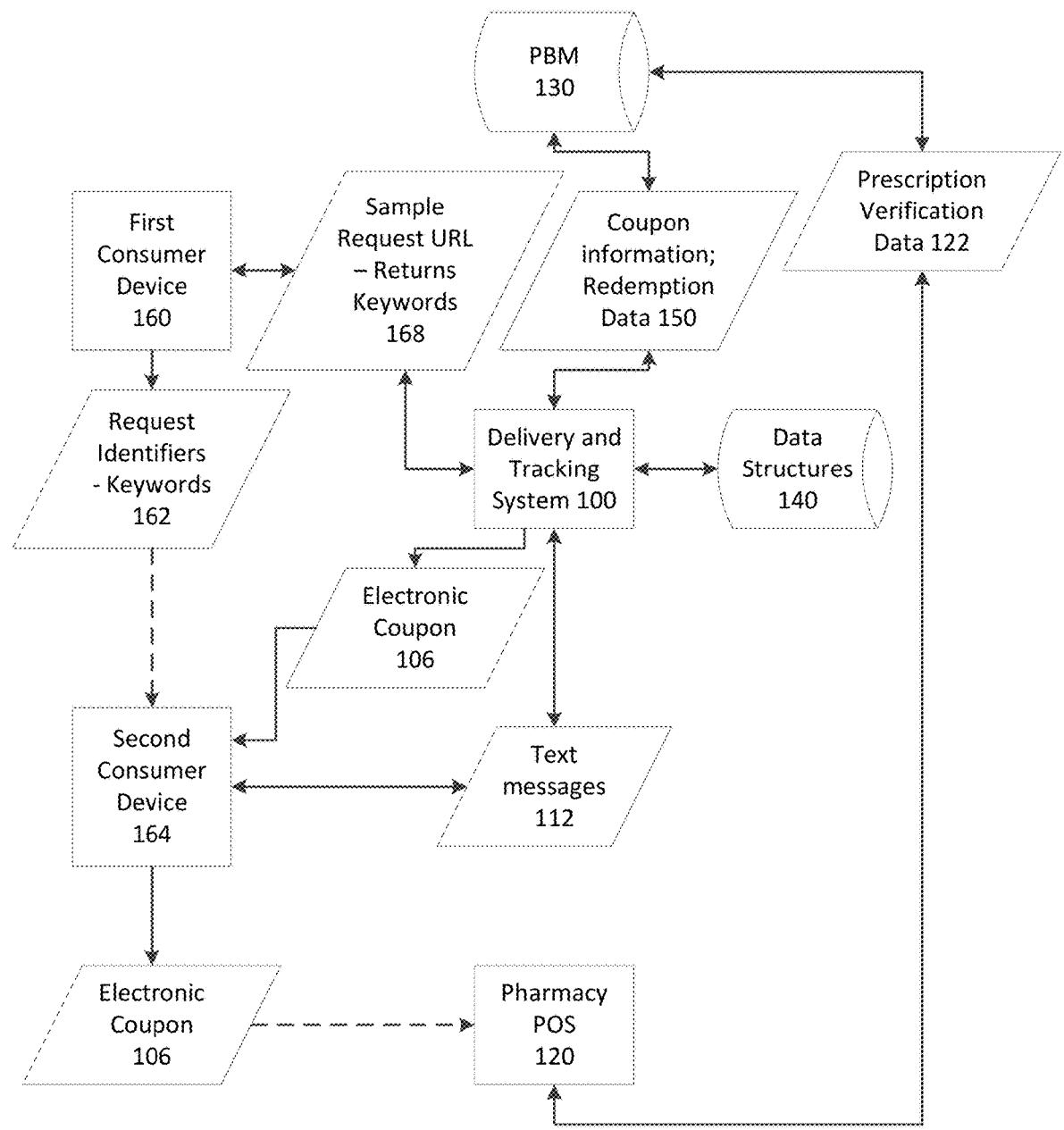
FIG. 1B is a block diagram of an example implementation of a computer system for delivery and tracking of pharmaceutical samples.

In some implementations, such as shown in FIG. 1B, the delivery and tracking system 100 can generate unique resource identifiers for accessing a resource accessible on a computer network, and a set of request identifiers associated with the link. In this example, the resource identifiers are referred to as sample request URL's (or URI's) or links, and the set of request identifiers are referred to as keywords associated with the link. Each sample request URL behaves similar to a sample pad, in that each sample request URL will have a series of associated keywords. The resource may be part of the delivery and tracking system 100, or a separate coupon server. In this example, a coupon server is described as part of the delivery and tracking system 100.

In some implementations, when the sample request URL is accessed as indicated at 168, for example by a doctor or other entity from a first consumer device 160, the coupon server checks to see if a coupon count is less than or equal to a number of budgeted coupons. If so, the coupon server returns to the first consumer device a request identifier at 168 to issue to a patient, such as a keyword and instructions on where to send the keyword in order to obtain an electronic coupon. If the coupon count is greater than then the number of budgeted coupons, then when the sample request URL is accessed, the delivery and tracking system will return a message indicating that no more coupons can be issued.

The request identifier 162, e.g., keyword and instructions, is communicated to the patient, for example via a digital communication channel such as email, electronic message on a social media platform, text message, or other communication channel. It should be understood that, in the context of the description of an example implementation a specific form of communication may be mentioned herein, a variety of possible forms of communication can be used, and the invention is not limited to a specific form of communication. A second consumer device 164, such as a mobile phone used by a patient, is used by the patient to send a message, such as a text message 112, including the received keyword to the delivery and tracking system 100, such as to the text number previously provided by the doctor or otherwise received. In some implementations, the keyword can be entered in a form for a website on a client browser. The delivery and tracking system 100 processes the message with the keyword, such as a text message 112, to provide an electronic coupon 106 to the consumer device 104. In some instances before the electronic coupon is returned there is a consent process.

The electronic coupon on the consumer device can be presented by the patient at a pharmacy, for example, or other location, having a i) point of sale system 120 for redemption of the coupon and processing of the transaction, and ii) a connection to a computer system 130 that performs adjudication, such as a Pharmacy Benefit Manager server ("PBM"), hereinafter referred to as PBM 130. This computer system 130 determines, or adjudicates, whether the presented content, such as a coupon, is valid and authorized for use. The computer system 130 also may handle any additional data processing, such as handling payment, account balances, and the like. The point of sale system 120 exchanges data 122 with the PBM 130, to: a) verify that the coupon had not been previously used, b) determine the discount to be applied, c) optionally determine the patient's eligibility to receive the discount based upon the patient's insurance, the prescribing physician, or other criteria, and d) mark the coupon as now used if appropriate (or decrement the number of times the coupon can be used).

The delivery and tracking system 100 maintains several data structures 140 to track requests for sample coupons, the delivery/viewing of sample coupons, redemption of sample coupons, and communicates with a PBM system 130 to exchange information 150 about coupons and coupon redemption (such as the unique identifier associated with a single-use coupon or the dispensing pharmacy's zip code).

Figure 6:
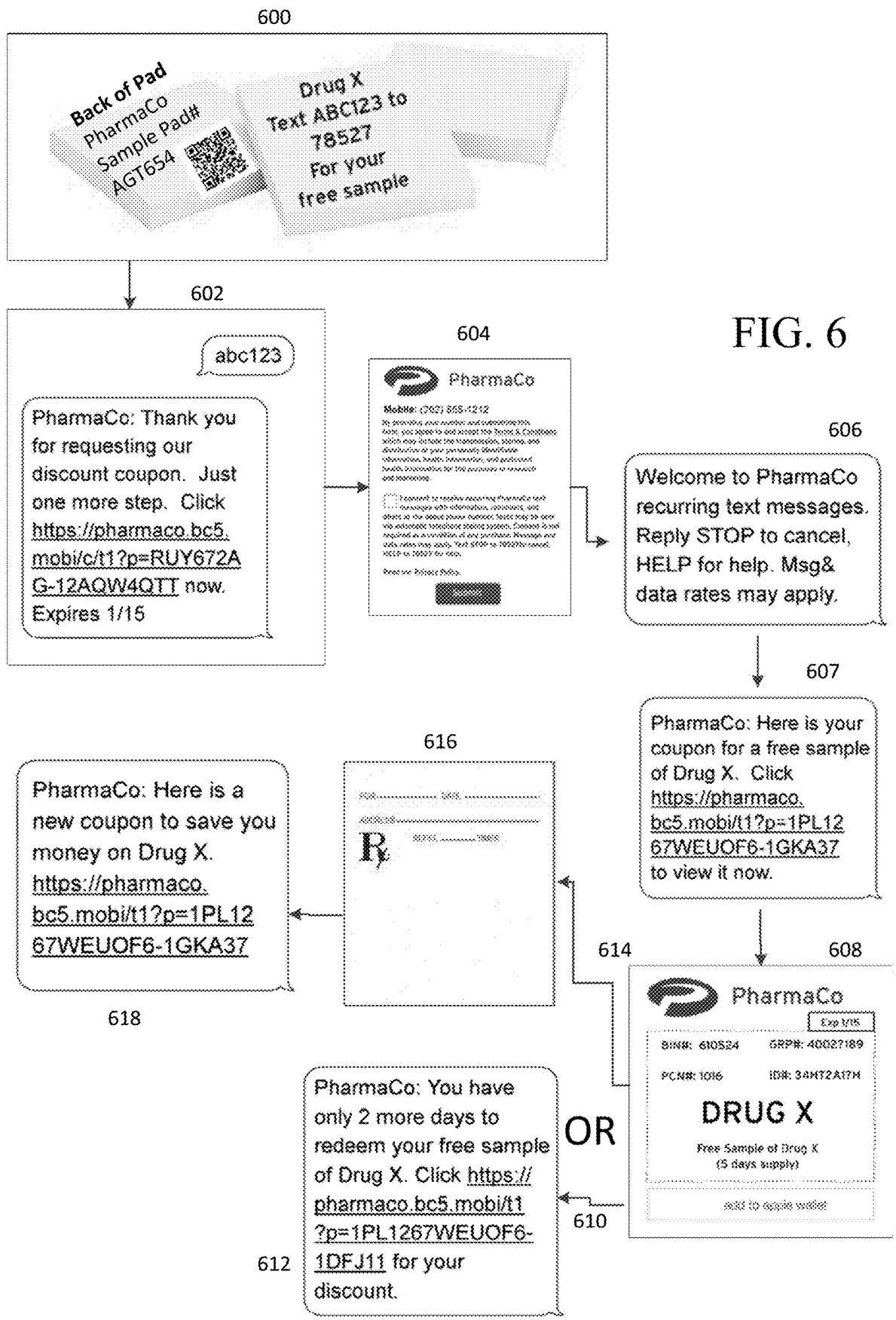
FIG. 6 is an illustration of example content delivered to consumer devices.

FIG. 6 is an illustration of an example consumer experience and example content that can be generated in text messages and other content for display on the consumer device when the consumer is interacting with the system.

In FIG. 6, illustrative examples of sample pads are shown at 600. At 602 is shown illustrative displays on the consumer device of text messages exchanged when the consumer texts "abc123" (as shown at top of 602) to "78527" (the number shown on the pad at 600) and receives back a text message (as shown at bottom of 602) with a link to a registration page for the pharmaceutical company. At 604 is shown an illustrative example of a registration page which is opened in a browser application and displayed on the consumer device when the link is activated. In this example, the user registers with the pharmaceutical company to authorize exchanging text messages, to authorize the pharmaceutical company to store the patient's Personal Health Information, and to receive a coupon. At 606 is shown a text message of an acknowledgement of the completed registration in the text message application and displayed on the consumer device. After registration is completed, in some implementations the electronic coupon also is delivered to the browser application of the consumer device. In this implementation as shown at 607, a second text message is sent with a link to the electronic coupon. Such a link is an example of a content identifier. In response to the consumer activating the link, the electronic coupon is delivered to and displayed in a browser application on the consumer device. At 608 is shown an illustrative electronic coupon as delivered to and displayed on the consumer's mobile device. The displayed electronic coupon is an example of the instance of digital content. In some implementations, a second message as shown in 607 would contain the entire electronic coupon details including the content identifier (e.g., MMS, or RCS). At 612, a reminder text message can be sent to the consumer device to remind the patient to use the coupon before the coupon expires. The reminder text message can include a link that, when activated, causes the electronic coupon to be delivered to and displayed in the browser application on the consumer device. At 616, the electronic coupon on the consumer device can be presented along with a prescription to a point of sale (e.g., a pharmacy) which has a connection to a PBM to verify the coupon. After redemption, the coupon server, the tracking system 100, or other computer system, such as a computer system managed by the pharmaceutical company, may send text messages or other communications to the consumer device (as shown at 618), offering additional coupons.

Data Structures

The delivery and tracking system 100 described herein utilizes a number of data structures 140 to support providing the intended functionality. An illustrative, example implementation includes the data structures shown in FIGS. 2 and 3, which are described below.

Referring to FIG. 2, a coupon data structure (200) stores, for each coupon for a kind of sample and associated with a coupon identifier (e.g. "Coupon 1"), common numbers associated with the coupon which define the discount being provided (e.g., Group, BIN, and PCN) for the kind of sample, the name of the medication ("Drug 1"), terms of the coupon, and any other information to be stored for the coupon.

A coupon code data structure (202) stores, for each coupon and associated with the coupon identifier, a set of unique identifiers. Each coupon identifier (e.g. "Coupon 1") indicates a type of coupon, whereas each unique identifier (e.g., "unique ID 1" indicates a unique instance of that type of coupon). For each coupon identifier, there can be multiple coupon identifier/unique identifier pairs. This data structure also can be used to track redemption information, such as a count.

A coupon code keyword data structure (204) stores, for a given keyword (e.g., "Keyword 1"), a coupon identifier and unique identifier with which the keyword is associated. The keywords are examples of request identifiers.

A coupon sample pad data structure (206) stores, for a given pad identifier (e.g., "Pad 1"), a keyword with which that pad identifier is associated. A pad identifier can be associated with multiple keywords.

A coupon URL/keyword data structure (208) stores, for a given sample request URL, a keyword with which that sample request URL is associated. The sample request URL is an example of a resource identifier. A sample request URL can be associated with multiple keywords. While a URL is commonly known as a "uniform resource locator" or a web address on the internet, as used herein it can represent any kind of unique identifier for a resource accessible on a computer network. The term as used herein can include, but is not limited to, any form of uniform resource identifier (URI) as defined by Internet standard RFC 3986, 6874, or 7320, or other string of characters that uniquely specifies a resource accessible on a computer network.

Referring to FIG. 3, a physician data structure (300) stores, for each physician and associated with a physician identifier (e.g., "Physician 1"), information about the physician. This information can be any information that can be useful about the physician, such as the physician's National Provider Identifier number (NPI #), a zip code, email address, other address or contact information, etc.

A sales representative data structure (302) stores, for each representative and associated with a representative identifier (e.g., "Rep1"), information about the sales representative, such as an employee identifier, company affiliation, zip code, other address or contact information, etc.

A sales representative and physician data structure (304) stores, for each representative and associated with a representative identifier (e.g., "Rep1"), a physician identifier identifying any physician with whom the sales representative is associated. A sales representative can be associated with multiple physicians. A physician can be associated with multiple sales representatives.

A distributed pad data structure (308) stores information about the sales representative and physician to whom sample pads are distributed. This example data structure associates, with a sales representative using the representative identifier, a pad identifier for any sample pad distributed to that sales representative. When that sample pad is distributed to a physician, the physician identifier is associated with the representative identifier and the pad identifier. Generally, a pad identifier should only have one associated sales representative identifier and one associated physician identifier. The pad identifier can be any data that uniquely identifies a set of printed items, such as a sample pad. FIG. 7 is a drawing of example content on a sample pad, and example content on a corresponding registration page for sales representatives to associate the sales representative, pad number, and physician.

Figure 8:
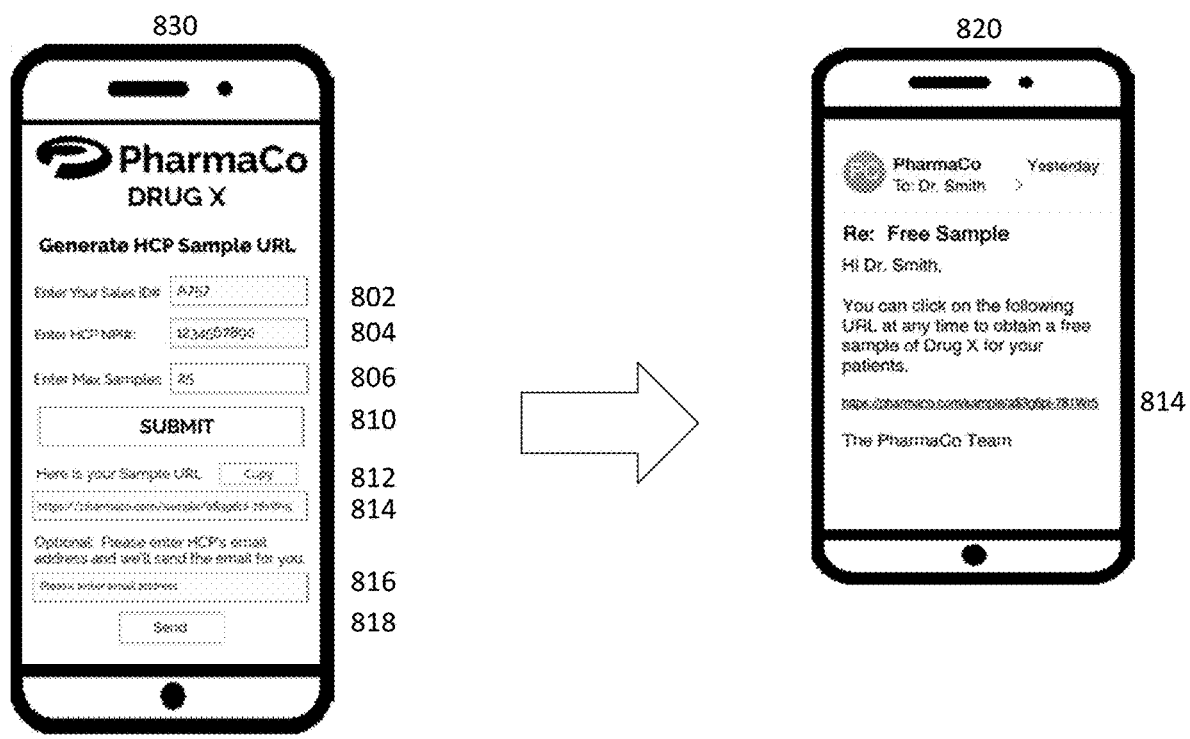

A sample request URL data structure (306) also stores information about the sales representative and physician to whom sample URL's are distributed. This example data structure associates, with a sales representative using the representative identifier, a unique sample request URL distributed by that sales representative to the given physician or physician's practice, a budget indicating how many unique coupons can be distributed with that particular sample request URL, and a count indicating the number of times the sample request URL has been accessed to request a coupon. When that sample request URL is generated and distributed to a physician, the physician identifier is associated with the representative identifier and the sample request URL. Generally, a sample request URL should only have one associated sales representative identifier and one associated physician identifier. 830 in FIG. 8 illustrates an example input screen that collects the physician identifier, representative identifier, and budget and generates the sample request URL and causes the Coupon Server to store these pieces of data into the sample request URL data structure A consumer data structure (310) stores information about how to contact a consumer. In this example, a consumer is identified by a phone number (e.g., "Phone 1"), which is associated with a telephone carrier.

A consumer SMS data structure (312) stores information for tracking delivery of coupons to consumers. Each message (e.g., "Message 1") sent using this system to a consumer, in this example using SMS text messages, is associated (using a message identifier) with the phone identifier, identifying the consumer to whom the message is sent, a coupon identifier of any coupon sent, a timestamp for when the message was sent or received or otherwise processed, and any content associated with the message.

A consumer coupon view data structure (314) stores information for tracking views of coupons by consumers. Each view of a message is associated, using a view identifier (e.g., "View 1"), with a phone identifier, identifying the consumer viewing the message, a coupon identifier of the coupon viewed, a timestamp indicating when the view occurred. An IP address, device, location, or other information about the context in which the coupon was viewed also can be stored.

Figure 4A:
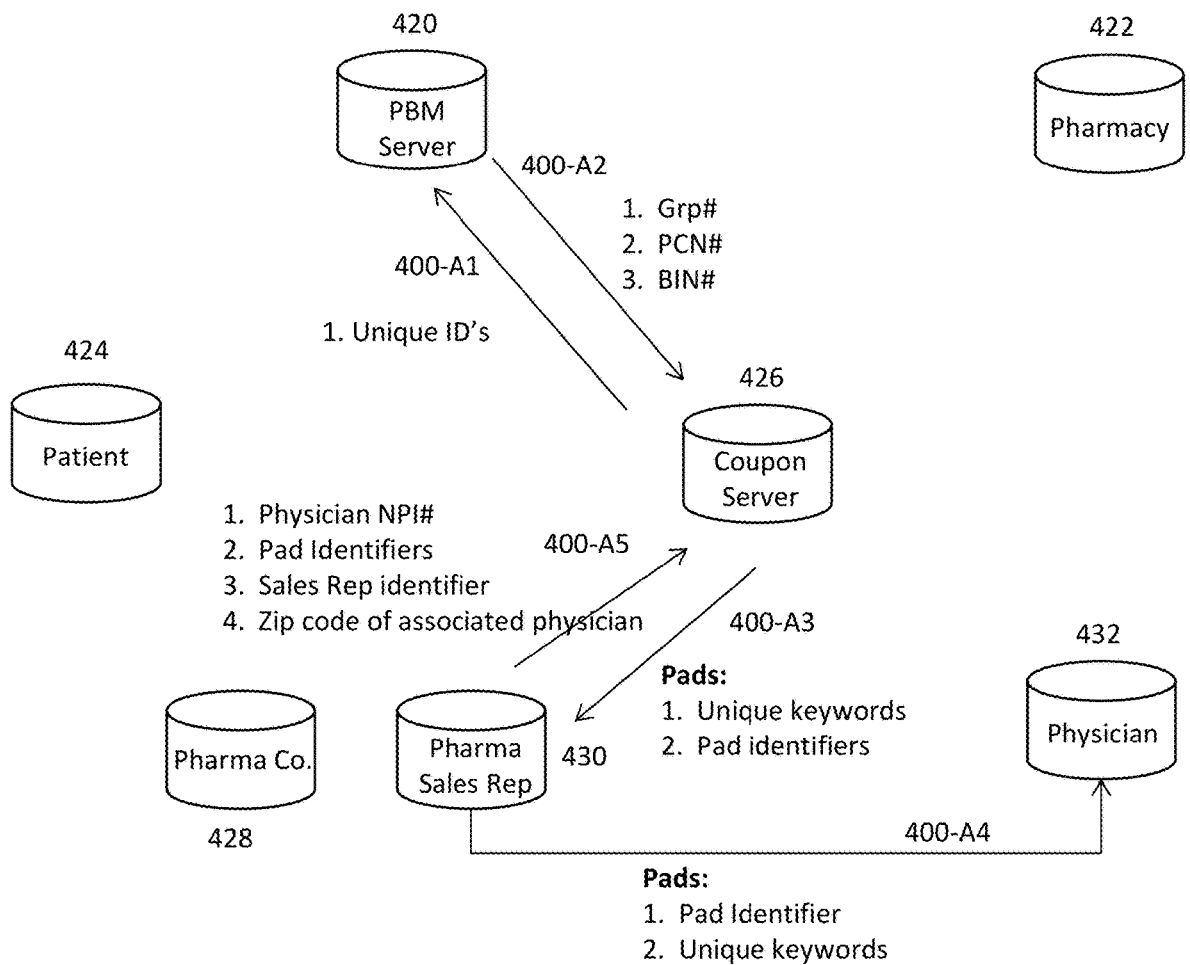

FIG. 4A—System Setup/Configuration

The PBM Server is a server computer that a) generates a group of 3 numbers (BIN #, PCN #, and Group #), b) stores sets of 4 numbers (BIN #, PCN #, Group #, and Unique ID #) ("4 Rx Numbers") and c) when contacted by a participating pharmacy's server with a set of 4 Rx Numbers, returns to the pharmacy server i) whether the 4 Rx Numbers are valid for use with a prescription and ii) the discounted amount the patient should pay for their prescription. The PBM Server also d) ensures that a set of 4 Rx Numbers can only be used to obtain a single discount, and e) returns to the Coupon Server (as defined below) any Unique ID #'s (and any other of the 4 RX #'s that identify the specific offer that was redeemed) that have been used to provide a discount on a filled prescription. Commercial providers of such systems include ProCareRx in Atlanta and CitizensRx in Chicago.

The Coupon Server 426 corresponds to the delivery and tracking system in FIGS. 1A and 1B and is a server computer that issues single use coupons, obtains end-user consent, delivers text messages, presents coupons to end users, and delivers reporting services.

The data flows in drawing 4A shows the initial setup for the system. Initially, the PBM Server sends to the Coupon Server the Rx Numbers for the Group #, PCN #, and BIN #for the coupon at 400-A2 (Note, in some cases the PBM Server may not send the PCN #or the Group #). Next, the Coupon Server will generate a set of Unique ID #'s for a specific coupon and provide them to the PBM Server 420 at 400-A1. The Coupon Server then combines the 3 Rx numbers for Group #, PCN #, and BIN #with the with set of Unique ID #'s to create sets of 4 Rx Numbers. The 4 Rx Numbers will allow the PBM Server to calculate the appropriate discount when a patient presents these numbers at a participating pharmacy and the pharmacy server contacts the PBM Server to inquire about the value of the coupon/discount. In some implementations, the PBM server can generate the 4th set of Unique ID numbers and deliver them along with the Group #, PCN #and BIN #to the Coupon Server.

Next, the Coupon Server generates a random, unique alphanumeric string (ex. ABC123, XYZ456, L1N56M, each a "Keyword") associated with each set of 4 Rx Numbers so that when the Coupon Server receives an incoming request containing one of the Keywords, it is able to return the associated set of 4 Rx numbers.

The Coupon Server then generates files containing a Sample Pad Identifier (a unique string of alphanumeric characters, an example of a pad identifier herein) and a set of Keywords. Each of these files is then delivered to a printing device that prints a set of items, such as a pad of small pieces of paper or other suitable material, with each piece of paper having one of the Keywords printed on the front of it (along with instructions to text in the Keyword to a short code, as defined below, to obtain a coupon) and the Sample Pad Identifier printed on the back (each a "Sample Pad"). Such a pad may be in the form of a set of POST-IT-style notes or other adhesive or perforated pieces of paper in the form of a pad allowing individual pieces of paper to be removed. The Coupon Server may generate one or more of these files for a given coupon and the printer may print one or more Sample Pads for each coupon. In some implementations, the Coupon Server can turn these files into emails containing sets of short code/keyword pairs. These emails could be sent electronically to an HCP who could then share the short code/keyword pair with a patient so the patient can text in the specified keyword to the specified short code to receive the coupon. Similarly, the Coupon Server could assign one or more of these files to each physician known to the Coupon Server and known physicians could log into the coupon server to obtain a short code/keyword pair to share with a patient.

In some implementations, the Coupon Server generates sample request URLs as shown in FIG. 8, 814, which when accessed as shown in FIG. 9, 930, display a unique keyword along with instructions to text in the Keyword to a short code (906), as defined below, to obtain a coupon. These sample request URLs (814) are distributed to HCPs who access the sample request URLs in order to receive a short code/keyword pair which is then shared with a patient so the patient can text in to receive the coupon.

At 400-A3, pharmaceutical company sales representatives receive one or more physical Sample Pads. When a sales representative meets with a HCP, the sales representative gives the HCP or HCP practice a Sample Pad at 400-A4, and subsequently at 400-A5, enters data into the Coupon Server including, but not limited to the Sample Pad Identifier, HCP's National Provider Identifier (NPI #) or name (or other related identifier), and zip code, and the Sales rep's identifier. This will allow the Coupon Server to associate each Sample Pad with a particular HCP so that summary reporting by HCP or HCP practice can later be generated. In some implementations as shown in FIG. 7, each Sample Pad can have other unique markings such as a QR code (704) indicating a Sample Pad Identifier that, when scanned by a mobile phone or similar device, causes the device to open a web page from the Coupon Server (706) which shows a prepopulated, non-editable field with Sample Pad Identifier, and which prompts the sales representative to enter any other information, such as the HCP's National Provider Identifier (NPI #) or name (or other related identifier), and zip code, and the sales representative's identifier, which are then associated with the Sample Pad Identifier in the data structures.

In some implementations, pharmaceutical company sales reps access a web site 830 which in turn accesses the Coupon Server to generate sample request URLs (814). The sales representative enters data into the Coupon Server including, but not limited to the HCP's National Provider Identifier (NPI #) or name (or other related identifier), the maximum number of samples that can be distributed by the sample request URL, zip code, and the Sales representative's identifier. This will allow the Coupon Server to associate each sample request URL with a particular HCP so that summary reporting by HCP or HCP practice can later be generated. The sales representative can then share the sample request URL with an HCP as shown at 820.

Figure 4B:
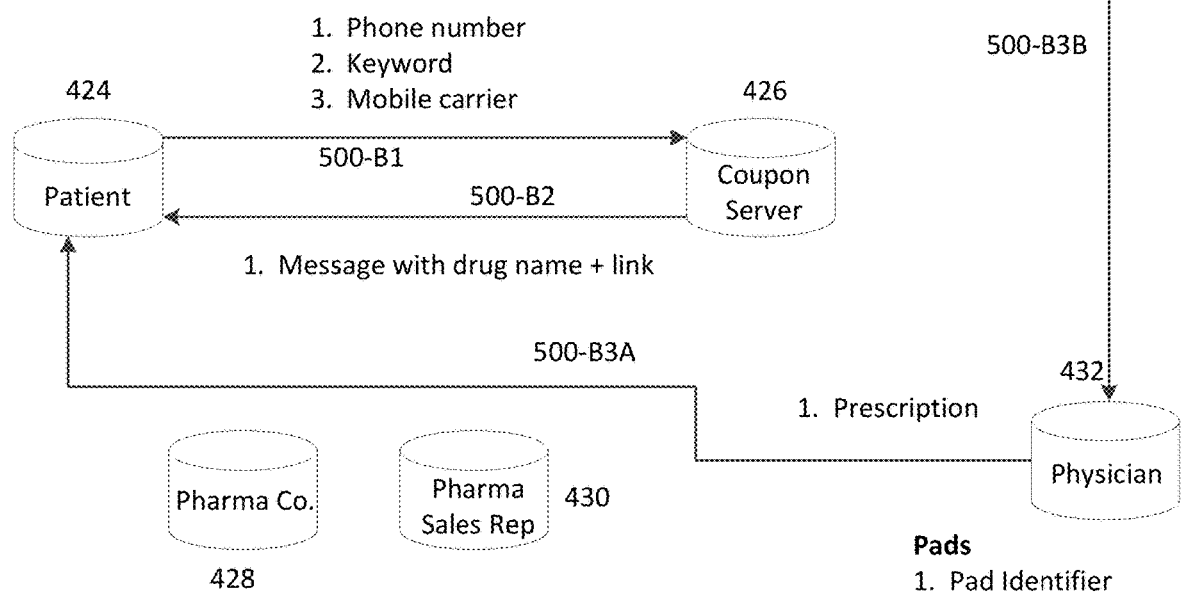

FIG. 4B illustrates what happens when the patient requests a coupon and that coupon is delivered to the patient.

When an HCP who has received a Sample Pad wants to provide a patient with a sample, the HCP provides the patient with one of the sheets of paper from the Sample Pad provided by the sales rep. At 500-B1, the patient texts in the Keyword from the Sample Pad sheet (e.g., ABC123) using the text messaging application on his/her mobile device to text to a short code (5 or 6 numbers) or other number as instructed. The Coupon Server, which is listening on the short code for Keywords, receives the Keyword and checks to see if the Keyword has already been received. If the Keyword has not already been received, then the Coupon Server checks to see if the mobile number that sent in the Keyword has already received a coupon for this specific product. If the mobile number has not previously sent in a different Keyword for this product and no other mobile number has sent in this Keyword, then the Coupon Server issues a coupon for the product and sends the patient a text message with a link to the coupon at 500-B2. If the Keyword has already been received from a different mobile number or this mobile number has already texted in a different Keyword for this product, then the Coupon Server communicates an error message to the patient, such as by sending an electronic message or displaying error content on a screen. At the same time, the HCP either gives the patient a prescription at 500-B3A for the medicine or sends the prescription electronically from the electronic medical record system to the pharmacy at 500-B3B. In some implementations, the HCP uses their electronic medical records (EMR) system to select one or more medication sample coupons to provide to the patient. The EMR system then submits a request to the Coupon Server and the Coupon Server sends the patient a message/notification with a link that when activated, displays a list of all of the sample coupons selected by the HCP.

In some implementations, when an HCP who has received a sample request URL wants to provide a patient with a sample, the HCP accesses the sample request URL as shown at 930. If the count of distributed coupons (the CurrentCount) at 902 is less than the Budget for the sample distribution URL, the Coupon Server generates unique instructions for how to obtain the coupon, increments the CurrentCount, and displays the instructions for how to obtain the coupon. The HCP then shares the instructions for how to obtain the coupon with the patient as shown at 910. The HCP can use any one of a number of methods for sharing this information with the patient including, but not limited to email, social channel, text, voice, or print (via US Mail or equivalent). The balance of the process is similar to that described above beginning with 500-B1.

FIG. 4C illustrates what happens when a patient views and accepts a consent form.

Using the text message application on their mobile device, the patient clicks the link in the text message at 600-C1 (thereby launching the web browser on the mobile device), and if the Coupon Server has no record of the mobile number accepting a consent form for this coupon, then the Coupon Serve presents the patient with a consent form in the web browser. The patient's mobile number is automatically associated with the consent form, as a pre-populated, non-editable field, and may or may not be displayed to the patient. As part of the consent form, the patient can opt-in to receive follow-on text messages (or emails). If the patient does not submit the consent form, the process stops. If the patient submits the consent form to the Coupon Server by taking an action such as clicking a button on the form labeled "Submit", then the Coupon Server displays the coupon in the patient's web browser and the process continues on to 4D, below. In some implementations, after the consent form is submitted, the Coupon Server could deliver to the patient a new text message which contains a link to the coupon. The coupon can be stored in a digital wallet, such as an APPLE WALLET as illustrated in FIG. 4I. In some cases, a wallet of coupons, or list of one or more coupons could be displayed when the patient clicks the link at 700-D1. This list of coupons could be for all prescription-based products, all non-prescription based products, or a combination of both. If a list of coupons is presented when the patient clicks on the link at 700-D1, then the patient may scroll or click additional times to view each of the individual coupons. Coupons can be issued by the Coupon Server at the time of delivery of the text message in Step 500-B2 in FIG. 4B or at the time the patient clicks the link in step 600-C1 in FIG. 4C.

FIG. 4D illustrates what happens when a patient views a coupon.

At Step 700-D1, the patient views the coupon/discount in the web browser on their mobile device after submitting the form at 600-C1. To do this, the consumer device sends a request to a server, in response to which the server returns data (700-D2) representing a view of the coupon. The coupon/discount displays the 4 Rx Codes (Group #, PCN #, BIN #and Unique ID #) that was associated during system setup/configuration with the Keyword texted in by the patient. Now that the consent form has been submitted, any time the patient clicks the link in the original text message at 500-B2, the Coupon Server displays the coupon in the patient's web browser on the mobile device without requiring the patient to view or accept the consent form again. In some implementations, the patient could click on a link in a message delivered after the form was submitted.

FIG. 4E illustrates what happens when a reminder to redeem is sent.

Each time a coupon is redeemed, the PBM Server delivers to the Coupon Server a unique set of 4 Rx Numbers indicating that the coupon that has been redeemed (or just the Unique ID #), allowing the Coupon Server to, among other actions, deliver reminders based upon the redemption status of a coupon. If the Coupon Server does not receive from the PBM Server a set of 4 Rx Numbers that was issued by the Coupon Server, then that will indicate to Coupon Server that the coupon was not redeemed. If the patient opted in for reminder messages at 600-C1, the Coupon Server will send the patient via text message or email (or push message, RCS, MMS, or some other communication method) a reminder to redeem the coupon.

Figure 4F:
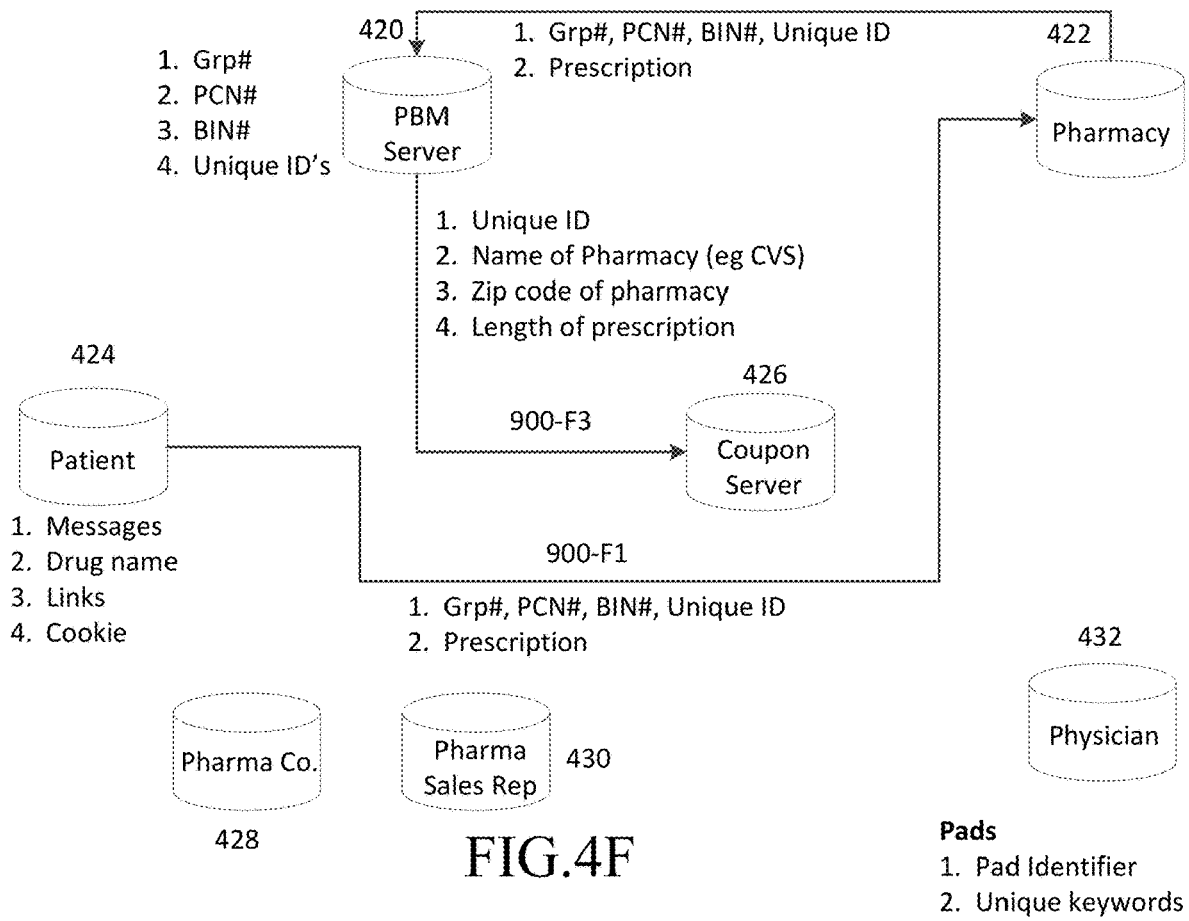
Figure 4I:
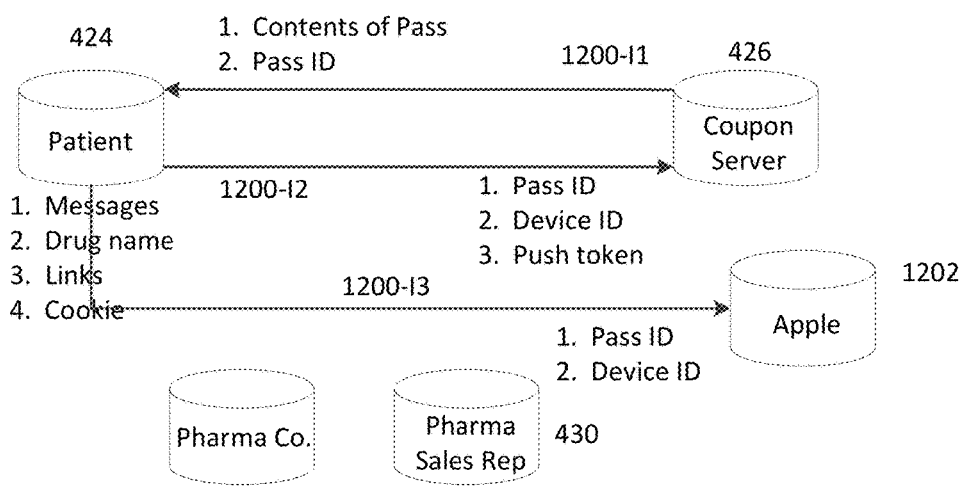

FIG. 4F describes a redemption process.

At 900-F1 the patient goes to the pharmacy with the prescription they received at 500-B3A or 500-B3B and the coupon they viewed at 700-D2 and receives their medication free of charge (or purchases the medication at a discount). As part of this process, the Pharmacy Server contacts the PBM Server with the 4 Rx Numbers at 900-F2 to see if the coupon is valid and has not been used before. If the coupon is valid and has not been used before, then the PBM Server tells the Pharmacy Server the coupon is valid and the value of the coupon. The patient then pays for the medication (the amount paid by the patient could be $0), takes delivery of the medication, and the Pharmacy Server confirms the transaction with the PBM Server which marks the coupon as redeemed so that if the same set of 4 Rx Numbers are presented again at any participating pharmacy's Pharmacy Server and that server contacts the PBM Server to validate the coupon, the PBM Server will inform the Pharmacy Server that the coupon is no longer valid.

After the coupon has been redeemed, the PBM Server at 900-F3 contacts the Coupon Server and indicates that a specific set of 4 Rx Numbers (or just the Unique ID #) has been redeemed and optionally delivers additional information such as the name of the pharmacy that redeemed the coupon, the length of the prescription (or other data that will allow the Coupon Server to calculate how many days of medication was received by the patient), zip code of redeeming pharmacy, time and date of redemption, and other relevant data. After the Coupon Server receives the 4 Rx Numbers indicating the coupon has been redeemed, if/when the patient attempts to view the coupon by clicking the link on their text message application on their mobile device, the Coupon Server will then display the coupon and indicate on the face of the coupon that the coupon has been redeemed. For example, the 4 Rx numbers could be removed and a message stating that the coupon had been redeemed at a specific date and/or time could be placed on the face of the coupon. If the coupon that was issued was a multi-use coupon, then the number of remaining uses or balance could be updated on the visible portion of the coupon. Additionally, the coupon server could send a message back to the referring physician that the coupon had been redeemed, thereby providing them with insight into whether the patient was following their instructions.

FIG. 4G illustrates sending redeeming patient another coupon.

If the patient opts in for follow-on messages at 600-C1, the Coupon Server will optionally send the patient a text message (or email) containing a link to one or more additional coupons at 1000-G1. The timing and content of these messages can be sent using the information the Coupon Server received from the PBM Server. For example, the Coupon server can use the data it received from the PBM Server regarding the number of days of medication dispensed from the last coupon to know when to send the reminder to use the next coupon.

FIG. 4H illustrates reporting.

After a number of sales reps have distributed the Sample Pads and a number of patients have requested coupons and redeemed them, at the request of a user of the Coupon Server, the Coupon Server will be able to provide reporting back to the pharmaceutical company reporting on activity at 1100-H1 such as:

a. #of coupons requested by Physician NPI #and Sales Rep
b. #of coupons redeemed by Physician NPI #and Sales Rep
c. #of coupons requested, viewed, and redeemed.
d. #of initial coupons distributed to HCP's, initial coupons requested, initial coupons redeemed, and follow-on/ additional coupons redeemed Referring now to FIGS. 8 and 9, an example of a contactless approach to delivering content, such as the sample pad data without using physical pads of paper, to physicians and from physicians to patients will now be described.

FIGS. 8 and 9 show user interfaces on mobile devices used by sales representatives, health care providers, and patients. From the perspective of these users, the actions taken by these users, and their experience with the system, can be explained as follows.

FIG. 8, 830 makes use of the sample request URL data structure. At the time the sales representative ("rep") wants to provide a HCP with a personalized URL that can be used to issue patient sample request instructions (the sample request URL), the sales representative navigates to the Rep Sample Request Web Page 830, hosted on the Coupon Server using a web browser and enters the HCP's National Provider Identifier (NPI #) or name (or other related identifier), and zip code, the Sales rep's identifier, and a budgeted number of coupons that can be distributed by the HCP (802-806). When the sales representative presses the submit button 810 on the Sample Requesting Web Page, the Coupon Server generates the sample request URL 814 based upon the entered NPI #and rep ID and stores all of the entered information in the sample request URL data structure. The sample request URL is then presented to the sales representative. This Sample Requesting Web Page could also be presented in 3rd party software such as a sales automation system (like Veeva) which could make a real-time API call via the internet to the Coupon Server using the rep ID and NPI #present in the sales automation system. In this case, the API returns the sample request URL 814 to the 3rd party software for presentation to/copying by the rep. Returning to the Sample Requesting Web Page, the sales representative either copies the sample request URL 814 to the clipboard of his/her computer orb) presses a button on the Sample Requesting Web Page to automatically i) launch the sales rep's email client software to send the message including the sample request URL directly to the HCP or at 818 ii) request the Coupon Server to directly send the email to the HCP. In the case of a), the sales representative would launch his/her email client, compose an email to the HCP, and paste (or type) in the sample request URL as shown at 820. The sales representative then sends the email to the HCP.

After the HCP has received the email containing the sample request URL, the HCP can click on this URL at any time to obtain a unique set of sample request instructions to be shared with a patient as shown at 930. The HCP accesses the sample request URL and views web page 930. Then, when the HCP clicks on the Request button 904, the Coupon Server a) checks to see if there is any remaining coupon budget (CurrentCount) available for the sample request URL, if so, b) increments the CurrentCount counter in the distributed URLs data structure and displays the web page shown 900, c) generates a new keyword, and stores the keyword into the coupon URL/keyword data structure thus allowing the Coupon Server to associate the generated keyword with sample request URL (and via the sample request URL to the HCP's NPI #and sales rep ID), and d) displays a set of instructions including the keyword (906). The HCP can then provide the set of instructions (906) to the patient using any of several techniques. For example, the HCP can copy the instructions to a clipboard of his/her computer, whether by capturing text or an image or other data, and paste the instructions into an email or other digital form of communication such as a text message to be sent to the patient as shown at 910. Other forms of communication to the patient include printing the instructions, sending an image of the instructions, sending the instructions through a form a voice communication, social channels, or any other means of communication. If there is no remaining coupon budget (Budget−Current Count=0 in data structure 306) when the HCP clicks the sample request URL, then the Coupon Server will inform the HCP that no budget is left and optionally ask the HCP if they would like to request additional sample budget. In some implementations, the budget can be checked and the counter incremented i) when the patient views the coupon, allowing for the budget to be checked at the time the patient attempts to view the coupon, or ii) when the URL is sent to the patient, if the URL is sent by the Coupon Server via a digital communication method such as text message, PUSH message, email or other communication method.

The foregoing description is an example implementation of a computer system implementing these techniques. The various computers used in this computer system can be implemented using one or more general-purpose computers, such as client devices including mobile devices, client computers, server computers and database computers, which can be programmed to implement the functionality such as described in the example implementation.

Figure 5:
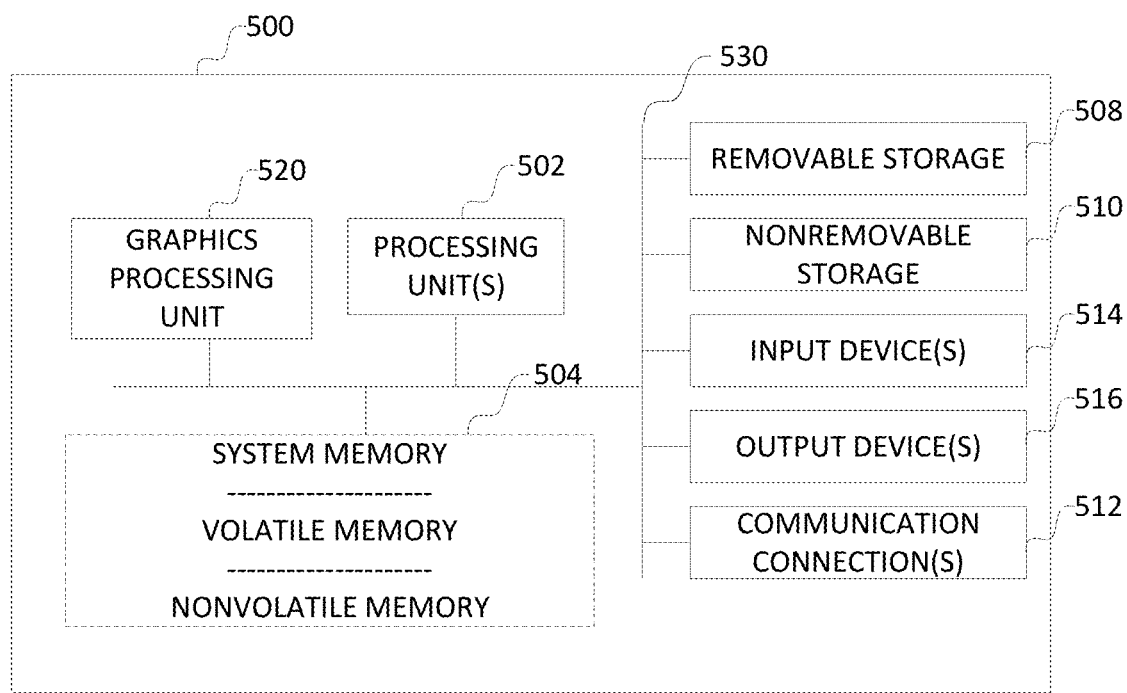
FIG. 5 is block diagram of a general purpose computer.

FIG. 5 is a block diagram of a general-purpose computer which processes computer program code using a processing system. Computer programs on a general-purpose computer generally include an operating system and applications. The operating system is a computer program running on the computer that manages access to various resources of the computer by the applications and the operating system. The various resources generally include memory, storage, communication interfaces, input devices and output devices.

Examples of such general-purpose computers include, but are not limited to, larger computer systems such as server computers, database computers, desktop computers, laptop and notebook computers, as well as mobile or handheld computing devices, such as a tablet computer, hand held computer, smart phone, media player, personal data assistant, audio and/or video recorder, or wearable computing device.

With reference to FIG. 5, an example computer 500 comprises a processing system including at least one processing unit 502 and a memory 504. The computer can have multiple processing units 502 and multiple devices implementing the memory 504. A processing unit 502 can include one or more processing cores (not shown) that operate independently of each other. Additional co-processing units, such as graphics processing unit 520, also can be present in the computer. The memory 504 may include volatile devices (such as dynamic random-access memory (DRAM) or other random-access memory device), and non-volatile devices (such as a read-only memory, flash memory, and the like) or some combination of the two, and optionally including any memory available in a processing device. Other memory such as dedicated memory or registers also can reside in a processing unit. This configuration of memory is illustrated in FIG. 5 by dashed line 504. The computer 500 may include additional storage (removable and/or non-removable) including, but not limited to, magnetically-recorded or optically-recorded disks or tape. Such additional storage is illustrated in FIG. 5 by removable storage 508 and non-removable storage 510. The various components in FIG. 5 are generally interconnected by an interconnection mechanism, such as one or more buses 530.

A computer storage medium is any medium in which data can be stored in and retrieved from addressable physical storage locations by the computer. Computer storage media includes volatile and nonvolatile memory devices, and removable and non-removable storage devices. Memory 504, removable storage 508 and non-removable storage 510 are all examples of computer storage media. Some examples of computer storage media are RAM, ROM, EEPROM, flash memory or other memory technology, CD-ROM, digital versatile disks (DVD) or other optically or magneto-optically recorded storage device, magnetic cassettes, magnetic tape, magnetic disk storage or other magnetic storage devices. Computer storage media and communication media are mutually exclusive categories of media.

The computer 500 may also include communications connection(s) 512 that allow the computer to communicate with other devices over a communication medium. Communication media typically transmit computer program code, data structures, program modules or other data over a wired or wireless substance by propagating a modulated data signal such as a carrier wave or other transport mechanism over the substance. The term "modulated data signal" means a signal that has one or more of its characteristics set or changed in such a manner as to encode information in the signal, thereby changing the configuration or state of the receiving device of the signal. By way of example, and not limitation, communication media includes wired media such as a wired network or direct-wired connection, and wireless media include any non-wired communication media that allows propagation of signals, such as acoustic, electromagnetic, electrical, optical, infrared, radio frequency and other signals. Communications connections 512 are devices, such as a network interface or radio transmitter, that interface with the communication media to transmit data over and receive data from signals propagated through communication media.

The communications connections can include one or more radio transmitters for telephonic communications over cellular telephone networks, and/or a wireless communication interface for wireless connection to a computer network. For example, a cellular connection, a Wi-Fi connection, a Bluetooth connection, and other connections may be present in the computer. Such connections support communication with other devices, such as to support voice or data communications.

The computer 500 may have various input device(s) 514 such as a various pointer (whether single pointer or multi-pointer) devices, such as a mouse, tablet and pen, touchpad and other touch-based input devices, stylus, image input devices, such as still and motion cameras, audio input devices, such as a microphone. The compute may have various output device(s) 516 such as a display, speakers, printers, and so on, also may be included. These devices are well known in the art and need not be discussed at length here.

The various storage 510, communication connections 512, output devices 516 and input devices 514 can be integrated within a housing of the computer, or can be connected through various input/output interface devices on the computer, in which case the reference numbers 510, 512, 514 and 516 can indicate either the interface for connection to a device or the device itself as the case may be.

An operating system of the computer typically includes computer programs, commonly called drivers, which manage access to the various storage 510, communication connections 512, output devices 516 and input devices 514. Such access generally includes managing inputs from and outputs to these devices. In the case of communication connections, the operating system also may include one or more computer programs for implementing communication protocols used to communicate information between computers and devices through the communication connections 512.

Any of the foregoing aspects may be embodied as a computer system, as any individual component of such a computer system, as a process performed by such a computer system or any individual component of such a computer system, or as an article of manufacture including computer storage in which computer program code is stored and which, when processed by the processing system(s) of one or more computers, configures the processing system(s) of the one or more computers to provide such a computer system or individual component of such a computer system.

Each component (which also may be called a "module" or "engine" or the like), of a computer system such as described herein, and which operates on one or more computers, can be implemented as computer program code processed by the processing system(s) of one or more computers. Computer program code includes computer-executable instructions and/or computer-interpreted instructions, such as program modules, which instructions are processed by a processing system of a computer. Generally, such instructions define routines, programs, objects, components, data structures, and so on, that, when processed by a processing system, instruct the processing system to perform operations on data or configure the processor or computer to implement various components or data structures in computer storage. A data structure is defined in a computer program and specifies how data is organized in computer storage, such as in a memory device or a storage device, so that the data can accessed, manipulated and stored by a processing system of a computer.

It should be understood that the subject matter defined in the appended claims is not necessarily limited to the specific implementations described above. The specific implementations described above are disclosed as examples only.

What is claimed is:

1. A computer system for delivering unique instances of a digital coupon, wherein the digital coupon is for redemption in connection with a medication requiring a medical prescription from a health care provider, the computer system comprising:
- a server computer comprising a computer storage medium storing a resource accessible by computing devices over a computer network using a resource identifier,
- a database accessible by the server computer and comprising a computer storage medium storing one or more records including data representing, for each of a plurality of health care providers authorized to issue coupons for the medication;
  - a respective unique resource identifier,
  - a respective set of unique keywords, comprising a plurality of unique keywords, for the health care provider, and
  - a respective budget for a number of keywords in the set of unique keywords that can be shared with the health care provider,
  - wherein the respective unique resource identifier and each unique keyword in the respective set of unique keywords for each health care provider are unique to the health care provider among the plurality of health care providers;
- a plurality of computing devices, each associated with a respective health care provider from among the plurality of health care providers; and
- wherein the server computer communicates with the plurality of computing devices over the computer network;
- a plurality of mobile devices, each associated with a respective individual from among a plurality of individuals, and wherein each mobile device has a respective mobile phone number;
- wherein the server computer communicates with the mobile devices using text messaging over one or more communication networks using the respective mobile phone numbers of the mobile devices;
- wherein each computing device of the plurality of computing devices includes a respective processing system and computer program instructions that, when processed by the respective processing system, cause the computing device to:
  - i. receive the respective unique resource identifier for the respective health care provider associated with the computing device,
  - ii. in response to input from the respective health care provider, access the resource from the server computer over the computer network using the respective unique resource identifier to submit a request for a unique keyword from the respective set of unique keywords for the health care provider, and
  - iii. after validation of the request against the respective budget for the health care provider by the server computer, receive, from the server computer over the computer network, the requested unique keyword;
- wherein each mobile device among the plurality of mobile devices includes a respective processing system and computer program instructions that, when processed by the respective processing system, cause the mobile device to:
  - i. receive a keyword and a text messaging number for sending a text message on the communication network to the server computer,
  - ii. in response to input from the individual, send a text message including the received keyword over the communication network from the respective mobile phone number of the mobile device to the received text messaging number of the server computer, and
  - iii. after validation by the server computer of the keyword and mobile phone number as valid for receiving the digital coupon, receive a unique instance of the digital coupon based on the sent text message; and
- wherein the server computer includes a processing system and computer program instructions that, when processed by the processing system, cause the server computer to:
  - i. in response to the request for the unique keyword received from the computing device for the one of the health care providers, validate that the one of the health care providers is authorized, based on the respective budget for the one of the health care providers, to receive the requested unique keyword, by:
    - a. determining whether the number of unique keywords previously sent to the one of the health care providers is less than the respective budget for the one of the health care providers, and
    - b. in response to a determination that there is no remaining budget for the one of the health care providers, returning a message over the computer network to the computing device for the one of the health care providers indicating that no more unique keywords are available to the one of the health care providers,
  - ii. after validation that the one of the health care providers is authorized to receive the requested unique keyword, send the requested unique keyword over the computer network to the computing device for the one of the health care providers and update the
  number of unique keywords sent to the one of the health care providers,
  - iii. monitor the text messaging number to detect text messages including keywords,
  - iv. in response to detecting a text message including a received keyword from one of the mobile devices, determine whether the one of the mobile devices is authorized to receive an instance of the digital coupon for the medication based at least on the received keyword and the respective mobile phone number of the one of the mobile devices,
  - v. after determining that the one of the mobile devices is authorized to receive the instance of the digital coupon for the medication;
    - a. assign a unique coupon code for a unique instance of the digital coupon to the respective mobile phone number of the one of the mobile devices, such that the unique coupon code for the unique instance of the digital coupon is unique to the one of the mobile devices among other instances of the digital coupon and other mobile devices,
    - b. send a text message to the one of the mobile devices including the unique instance of the digital coupon for the medication or a link to the unique instance of the digital coupon for the medication, and c. store one or more records in the database to associate: i. the respective mobile phone number of the one of the mobile devices, ii. the received keyword, iii. an identifier for the health care provider that distributed the received keyword, and iv. the unique coupon code for the unique instance of the digital coupon, whereby the unique instance of the digital coupon is unique to the respective mobile phone number of the one of the mobile devices, the health care provider, and the received keyword together, and whereby the mobile phone number, health care provider, and the received keyword are associated in the database; and a transaction processing computer system including an input system configured to receive, in connection with processing a transaction for the medication, the unique instance of the digital coupon as delivered to one of the mobile devices and an input indicating a valid medical prescription for the medication has been prepared for the individual associated with the one of the mobile devices by one of the health care providers.

2. The computer system of claim 1, wherein the server computer is further configured to generate the respective resources for the health care providers and distribute the respective unique resource identifiers for the respective resources to the health care providers.

3. The computer system of claim 2, wherein the unique resource identifier comprises a respective URL uniquely assigned to the health care provider.

4. The computer system of claim 1, wherein the server computer is configured to, after validation that the one of the health care providers is authorized to receive the requested unique keyword, generate the requested unique keyword, and store the requested unique keyword in the respective set of unique keywords for the one of the health care providers in the database.

5. The computer system of claim 1, wherein the server computer is further configured to:
   generate the sets of unique keywords and store the sets of unique keywords in the database; and
   after validation that the one of the health care providers is authorized to receive the requested unique keyword, select the requested unique keyword from the respective set of unique keywords for the one of the health care providers from the database.

6. The computer system of claim 1, wherein each unique keyword comprises a random, unique alphanumeric string.

* * * * *